United States Patent [19]  [11] 3,992,517
Lowke et al.  [45] Nov. 16, 1976

[54] DETECTION OF HEPATITIS B SURFACE ANTIGEN BY LATEX AGGLUTINATION

[75] Inventors: George E. Lowke, Gales Ferry; Bela Z. Horvath, Ledyard, both of Conn.

[73] Assignee: Pfizer Inc., New York, N.Y.

[22] Filed: Feb. 19, 1975

[21] Appl. No.: 550,949

[52] U.S. Cl. .............................. 424/12; 260/112 R; 260/112 B; 424/78; 424/86; 424/89; 424/93
[51] Int. Cl.² ................. G01N 31/02; G01N 31/06; A61K 39/12; A61K 39/42
[58] Field of Search ................... 424/12, 86, 89, 93; 260/112 R, 112 B

[56] References Cited
UNITED STATES PATENTS
3,838,144  9/1974  Leach .............................. 424/12 X OTHER PUBLICATIONS
Leach, British Med. J., 4, Dec. 1971, pp. 597–598.
Cayzer, The Lancet, May 18, 1974, pp. 947–949.
Fritz, J. of Immunology, vol. 108, Jan. 19, 1972, pp. 108–111.
Juji, Japan J. Exptl. Med., vol. 39, 1969, pp. 615–620.
Malin, Nature New Biol., vol. 235, Feb. 9, 1972, p. 182.
Dandliker, Biochemistry, vol. 6, No. 5, 1967, pp. 1460–1466.
Desmyter, Chem. Abs., vol. 79, 1973, pp. 287.

Primary Examiner—Albert T. Meyers
Assistant Examiner—A. P. Fagelson
Attorney, Agent, or Firm—Connolly and Hutz

[57] ABSTRACT

A diagnostic composition for the detection of hepatitis B surface antigen in blood serum which comprises an aqueous suspension of finely divided synthetic resin particles of substantially uniform size coated with purified antibody specific to hepatitis B surface antigen is employed in a differentiating method where rheumatoid factor, which may cause nonspecific reactions, is absorbed with latex beads coated with human gamma globulin.

4 Claims, No Drawings

DETECTION OF HEPATITIS B SURFACE ANTIGEN BY LATEX AGGLUTINATION

BACKGROUND OF THE INVENTION

The hepatitis B surface antigen (Australia antigen) discovered by Blumberg and associates, Bull. N.Y. Acad. Med., 40, 377 (1964) and the subsequent correlation with long incubation period hepatitis has stimulated much activity in screening blood donor populations in the interest of public health.

The use of antibody-sensitized latex particles reported in U.S. Pat. Nos. 3,085,875 and 3,551,555 has been specifically adapted for the detection of hepatitis B surface antigen in blood serum as described in The Journal of Immunology 108, No. 1, pages 108–111 (1972).

A sensitive but time-consuming radioimmune assay is described by Ling, C.M. and Overby, L.R., The Journal of Immunology 109, No. 4, pages 834–841 (1972) ).

There is a need, however, for an improved diagnostic method which is rapid, sensitive, and most importantly, reliable (minimal "false positives").

SUMMARY OF THE INVENTION

This invention is concerned with a diagnostic composition for the detection of hepatitis B surface antigen in human blood which comprises an aqueous suspension of finely divided synthetic resin particles of substantially uniform size coated with purified antibody specific to hepatitis B surface antigen. False positives are minimized by the addition of normal serum from the same species of animal as that from which the serum containing the antibody was obtained, and confirmation of all positive sera utilizing human hepatitis associated antibody, normal human serum control and a rheumatoid factor absorption reagent.

DETAILED DESCRIPTION OF THE INVENTION

The diagnostic composition of the present invention is designed to be highly sensitive and specific for the detection of hepatitis B surface antigen in human blood by (a) employing resin particles coated with purified antibody prepared from animals immunized with purified hepatitis B surface antigen and (b) minimizing false positives by the addition of normal serum from the same species of animal as that from which the serum containing the antibody was obtained, and (c) confirming all positive sera utilizing human hepatitis associated antibody for antigen neutralization, normal human serum control and a rheumatoid factor absorption reagent.

The diagnostic composition of the present invention comprises an aqueous suspension of finely divided synthetic resin particles coated with highly purified antibody specific to hepatitis B surface antigen. Preferably the particles are spherical polystyrene particles having a diameter of about 0.23 microns, but particles of polystyrene or other synthetic resins, e.g. acrylic resins, having uniform dimensions of from 0.05 to 2.0 microns may be suitable.

The antibody specific to hepatitis B surface antigen is preferably derived from serum obtained from mammals, e.g. humans, sheep, goats, rabbits or guinea pigs or from avian sources such as chickens or turkeys which contain the antibody or have been immunized with highly purified hepatitis B surface antigen obtained from human blood.

Guinea pigs or other animal species such as rabbits, goats, etc. are immunized with hepatitis B surface antigen purified by the method described in U.S. Pat. No. 3,838,144. A primary immunization with antigen in Freund's complete adjuvant in the foot pads is followed by repeated intraperitoneal, intramuscular, subcutaneous or intravenous inoculations of antigen with or without adjuvant. After pooling the sera collected from immunized animals, residual antibody to human serum proteins, if present, is removed by contacting the antiserum with normal human serum. The gamma globulin may then be isolated by precipitation with 14% aqueous sodium sulfate, dialyzed against aqueous phosphate buffered saline and preferably heated at 56° C. for about 30 minutes to destroy complement.

The antibody is further purified by the general methods described in The Journal of Immunology 106, No. 3, pages 589–597(1971) and Biochemistry 6, No. 5, pages 1460–1466 (1967). Specific hepatitis B surface antibody is purified from the absorbed animal sera (preferably guinea pig sera) by mixing the sera, in optimal proportions, with human sera containing hepatitis B surface antigen, incubating at 37° C. for one hour, then overnight at 4° C. The antigen-antibody precipitate thus formed is then washed twice in cold phosphate buffered saline to remove most residual nonspecific proteins. The antigen-antibody precipitate is then dissolved in cold 0.2 M acetic acid/2% sucrose, pH 2.3 or various molarities of chaotropic ions (e.g. 2.0 M sodium thiocyanate, pH 6.6). Those skilled in the art will recognize that other appropriate buffers to dissociate the antigen-antibody complexes may be employed. These dissociated antigens and antibodies are separated by centrifugation at 25,000–28,000 r.p.m. for 12–15 hours or at 30,000 r.p.m. for 4 hours on a continuous 10–40% sucrose gradient in the Bechman TI-15 zonal rotor. The rotor is unloaded by pumping 50% sucrose in to displace the gradient and 20 ml fractions are assayed for U.V. absorbance in a 1 cm. cell at 280 m$\mu$ and peak fractions are pooled to give a purified, specific antibody fraction and a purified antigen fraction Both fractions are then neutralized with 0.1 N NaOH. The antibody fraction is concentrated to the original serum volume and dialyzed overnight against glycine buffered saline. The purified antibody is then titered and standardized.

Sodium azide, 0.1%, may be added as a preservative for use in preparation of the diagnostic reagent. The antibody is optimally diluted by preparing small batches of the diagnostic reagent with various dilutions of the antibody and testing these against a panel of human sera known to contain hepatitis B surface antigen. The dilution giving the best performance against the panel when coated onto resin particles is selected for preparation of the diagnostic reagent.

The suitably diluted antibody is mixed with 0.2$\mu$ diameter polystyrene latex beads. After mixing for one to two hours, the beads are washed three times with glycine buffered saline and resuspended in glycine buffered saline.

The aqueous suspension preferably contains about 0.5% w/v of the resin particles but could contain from 0.1 to 3% w/v of the resin particles. For the preparation of the diagnostic reagent, the suspension preferably contains about 0.05% w/v of antibody thereto absorbed on the resin particles, but this can be varied in accordance with the concentration of particles. The proportion of antibody should be just sufficient to prevent auto-aggregation of the resin particles. For spherical polystyrene particles of 0.23 microns in diameter, this is about one-tenth of the weight of the particles.

The suspension preferably contains a stabilizer added after absorption of the antibody on the particles, e.g. an inert protein such a serum albumin at a concentration of, for example, 0.1% w/v.

According to a preferred embodiment of the invention, the diagnostic reagent also contains normal serum (i.e. serum which does not contain either the antibody specific to hepatitis B surface antigen or the antigen itself) obtained from the same species of animal as that from which the serum containing the antibody was obtained. The presence of such normal serum reduces substantially the proportion of false positives when the diagnostic reagent is used to detect hepatitis B surface antigen in blood samples. Preferably about 1 part of normal serum is included per 20 to 50 parts (by volume) of the aqueous suspension of resin particles coated with antibody. If normal serum from the same species of animal as that from which the serum containing the antibody was obtained is not included in the diagnostic reagent, about 10% of human sera which do not contain hepatitis B surface antigen will agglutinate the resin particles. This is probably due to the presence of substances in such human sera which react with other materials originating from the animal antiserum from which the antibody to hepatitis B surface antigen was obtained. If the normal animal serum is included, however, only between 1 and 3% of human sera will agglutinate the resin particles in the absence of hepatitis B surface antigen from the sera. This may be due to components in the normal animal serum being able to react with those substances in the human sera and so prevent them from causing agglutination of the resin particles.

A normal human serum control is provided which is produced from undiluted normal human serum shown to be negative for hepatitis B surface antigen by the latex reagent and by radioimmunoassay.

A positive control serum is prepared from a pool of known hepatitis B surface antigen positive human serum. The serum is heat treated at 60° C. for at least 10 hours to destroy infectivity of the virus and then twofold serially diluted in normal human serum. The dilution used for the product is the one giving a definite 1 + reaction with the latex reagent.

The diagnostic reagent system consists of the following component
  A. Screening Test System
    1. Hepatitis Associated Antibody absorbed on latex beads
    2. Positive Control Serum
    3. Negative Control Serum
  B. Confirmatory Test System
    1. Hepatitis Associated Antibody (Human)
    2. Normal Human Serum Control (negative for hepatitis B surface antigen)
    3. Rheumatoid Factor Absorption Reagent
    4. Confirmatory Test Diluent The hepatitis associated antibody (human) is produced from human plasma which contains antibodies to hepatitis B surface antigen. The plasma is received from various plasmaphoresis centers, is titered by gel diffusion, and is converted to serum by addition of calcium chloride and bovine thrombin. Gamma globulin is then prepared from the serum by precipitation with 16% sodium sulfate. After washing the precipitate in 14% sodium sulfate, it is dialyzed overnight against a low molarity phosphate buffer and passed through DEAE celluose which had been previously equilibrated with the same buffer. The purified gamma globulin is then standardized by concentration and dialyzed against phosphate buffered saline.

The rheumatoid factor absorbent reagent consists of latex beads coated with normal human gamma globulin. It is produced by making a standard solution of purified gamma globulin in glycine buffered saline, adding a suspension of 0.2 microns polystyrene beads and heating at 57° C for 15 minutes. The suspension is then diluted in glycine buffered saline.

The confirmatory test diluent is prepared by diluting a solution of 30% bovine serum albumin with phosphate buffered saline to a 5% protein concentration.

TEST METHODS

A. Preparation of Blood Sample

Serum is the preferred form of the blood specimen. If the test sample is of whole blood, it must first be treated to lyse the cells in it and prevent coagulation. For this purpose it may be treated with an aqueous diluent containing a non-ionic surfactant of the polyoxyethylated alkylphenol type, e.g. isooctylphenoxy-polyoxyethyl-ethanol (Triton X-100, Rohm & Haas Co.) and sodium citrate.

If the test sample is of blood plasma, it must contain an anticoagulant, e.g. any of the standard anticoagulants such as sodium citrate. It is advantageously also treated with the same aqueous diluent containing a non-ionic surfactant as for whole blood in order to lyse any residual cells present therein.

B. Reagents

1. Latex Reagent
  a. Specificity
    1. Determined by testing the reagent with the panel of positive and negative sera supplied by the Bureau of Biologics as well as a panel of 100 negative sera collected from normal volunteers.
  b. Reactivity
    1. Resuspend the reagent by vigorous agitation.
    2. To one of the test wells on the plastic test plate dispense 3 drops of positive control serum. To second adjacent well dispense 3 drops of negative control serum.
    3. To each sample dispense one drop of reagent.
    4. Mix completely using a separate mixer for each well.
    5. Rotate the plate on a mechanical rotator for 10 minutes at 150 rpm.
    6. Examine the mixtures over an indirect lighted viewbox.
    7. A clearly positive, weak (1$^+$) reaction should be observed with the positive control serum sample. No reaction should be observed with the negative control serum sample.
2. Positive Control Serum
  a. Reactivity
    1. The positive control serum is tested with the latex reagent to ensure a reactivity of 1$^+$.
3. Negative Control Serum
  a. Reactivity
    1. The negative control serum is tested with the latex reagent to insure a negative reaction.
4. Normal Human Serum Control a. Specificity 1. Confirmatory test is performed to ensure that it does not react with the latex reagent and that it does not inhibit hepatitis B surface antigen positive sera.

5. Hepatitis Associated Antibody (Human)

a. Reactivity

1. A gel diffusion titer is performed using a standard hepatitis B surface antigen.

b. Specificity

1. A use test is performed to determine if the serum will specifically inhibit hepatitis B surface antigen positive samples when utilized in the confirmatory test protocol.

6. Absorption Reagent a. Reactivity

1. The reagent is tested with sera containing Rheumatoid Factor to ensure that it will react with the factor and will partially absorb it out from sera containing it.

7. Confirmatory Test Diluent a. Specificity

1. The confirmatory test is performed utilizing the diluent to ensure that it does not react with the latex reagent and that it does not inhibit hepatitis B surface antigen positive sera.

C. Testing of Serum Samples (Screening Test)

1. Dispense 120 $\mu$l. serum into well on plastic plate.
2. Add one drop of Latex Reagent
3. Mix completely using a separate disposable mixer for each sample
4. Rotate the plate on a mechanical rotator for 10 minutes at 150 r.p.m.
5. Examine the mixtures over an indirect lighted viewbox.
6. Reactions are scored on a scale of 1$^+$ to 4$^+$ corresponding to increasing intensity of agglutination.

D. Confirmatory Neutralization Procedure

1. Specimens a. All speciments identified as positive in the screening test.

b. Positive Control Serum included as a weak positive specimen.

2. Procedure a. Label one disposable 10 × 75 mm test tube with the specimen identification number and "A". Label a second tube the specimen identification number and "B".

b. Add two drops (approximately 80 $\mu$l.) of Hepatitis Associated Antibody (Human) to the tube labeled A.

c. Add two drops of the Normal Human Negative control Serum to the tube labeled B.

d. Add 240 $\mu$l. of the test specimen to each of the tubes labeled A and B.

e. Mix contents of the tubes and incubate for 30 minutes at 37° C. in a water bath.

f. Test 120 $\mu$l. from tubes A and B using the screening reagents and procedures. For most relatively low titered positive samples, differentiation between specific and nonspecific positives can be made without further testing as the A sample will be nonreactive while the B sample remains positive, indicating specific inhibition by the human antibody. For those samples which are specific but higher titered as well as those which are nonspecific, further testing is required as detailed below.

g. For each tube requiring further testing, label and additional six tubes with dilutions from 1:4 – 1:128 and the specimen identification as well as A or B.

h. Add 200 $\mu$l. of the confirmatory test diluent to each tube, including the tubes which contain the patient's specimen and Human antiserum or Normal Human Serum, i.e., the original A and B tubes, making them approximately a 1:2 dilution.

i. Make twofold dilutions by transferring 200 $\mu$l. using separate micropipet tips for each tube and mixing well before removing samples.

j. Test 120 $\mu$l. from each tube using the screening reagents and procedures.

k. The titer obtained in row B (specimen and Normal Human Serum) must be fourfold (two tubes) higher than in row A (specimen and neutralizing hepatitis associated antibody (human) in order to consider the specimen as a specific hepatitis B surface antigen positive. In cases where both A and B titer is higher than 1:128, the dilution must be carried out further until an end point is determined.

Since a number of specimens containing Rheumatoid Factor will react with the latex reagent, it is necessary to differentiate those specimens containing both hepatitis B surface antigen and Rheumatoid Factor.

1. The presence of Rheumatoid Factor may be determined by testing the serum with the Rheumatoid Factor absorbing reagent (human gamma globulin coated latex) by mixing 120 $\mu$l. of the specimen and one drop of the absorbing reagent on a plastic slide and rotating for 5 minutes.

If the specimen contains Rheumatoid Factor, it may be absorbed out by adding 720 $\mu$l. of the specimen to a 10 × 75 mm test tube and dispensing six drops of the absorbing reagent into the tube. Mix well and incubate at room temperature for 15 minutes. Centrifgue at 3,000 r.p.m. for 5 minutes. Perform the confirmatory neutralization procedure on the absorbed specimen as detailed above.

PREPARATION OF PURIFIED ANTIBODY TO HEPATITIS B SURFACE ANTIGEN

Guinea pigs are immunized with hepatitis B srface antigen purified by the method described in U.S. Pat. No 3,838,144.

A primary immunization with antigen in Freund's complete adjuvant in the foot pads of guinea pigs is followed by two intraperitoneal inoculations of antigen without adjuvant. After pooling the sera collected from immunized animals, residual antibody to human serum proteins is removed if necessary by contacting the antiserum with normal human serum. The gamma globulin is then purified by precipitation with 14% w/v aqueous sodium sulfate, dialyzed against aqueous phosphate buffered saline and preferably heated at 56° C. for about 30 minutes to destroy complement.

The purified serum is mixed with human serum containing hepatitis B surface antigen, incubated at 37° C. for 1 hour, then overnight at 4° C. The antigen-antibody precipitate thus formed is then washed twice in cold phosphate buffered saline to remove most residual nonspecific proteins. The antigen-antibody precipitate is then dissolved in cold 0.2 M acetic acid/2% sucrose, pH 2.3 or chaotropic ions. The dissociated antigens and antibodies are separated by centrifugation at 25,000–28,000 rpm for 12–15 hours or at 30,000 rpm for 4 hours on a continous 10–40% sucrose gradient in the Beckman TI-15 zonal rotor. The rotor is unloaded by pumping 50% sucrose in to displace the gradient and 20 ml fractions are assayed for U.V. absorbance in a 1 cm. cell at 280 µ, and peak fractions are pooled to give a purified, specific antibody fraction which is then neutralized with 0.1 N NaOH. The antibody fraction is concentrated to the original serum volume and dialyzed overnight against glycine buffered saline. The purified antibody is then titered and standardized.

The antibody is optimally diluted by preparing small batches of the diagnostic reagent with various dilutions of the antibody and testing these against a panel of human sera known to contain hepatitis B surface antigen. The dilution giving the best performance against the panel when coated onto resin particles is selected for preparation of the diagnostic reagent.

PREPARATION OF DIAGNOSTIC REAGENTS

EXAMPLE I

A 30% w/v aqueous suspension of 0.23 µ polystyrene spheres manufactured by Dow Chemical is diluted to 8% w/v with glycine-buffered saline and dialyzed against glycine-buffered saline overnight. It is then immediately added to 9 volumes of purified guinea pig anti-serum containing the antibody to hepatitis B surface antigen (diluted to 0.05% w/v) and stirred constantly for 30 minutes. One volume of bovine serum albumin (1% w/v) is then added and finally sodium azide to give a concentration of 0.1% w/v in the final product.

EXAMPLE II

A 30% w/v suspension of polystyrene spheres (0.05–2.0 µ) is diluted to 8% with glycine-buffered saline and sterilized by addition of hypochlorite solution. It is then dialyzed against glycine-buffered saline to remove the hypochlorite. It is then added to 9 volumes of suitably diluted, purified guinea pig serum antibodies to hepatitis B surface antigen. The polystyrene suspension is added slowly with stirring which is continued for 1 hour. The polystyrene spheres are centrifuged, washed twice on the centrifuge with buffered saline and re-suspended to the original volume in buffered saline. Bovine serum albumin is added with stirring for 30 minutes. One-tenth of a volume of diluted diluted normal serum from non-immunized guinea pigs (diluted 1:3.5 with glycine-buffered saline) is added and the mixture again stirred for 30 minutes. Finally, the mixture is shaken vigorously to disperse any agglomerations of particles. All solutions used are sterilized by filtration and contains 0.1% w/v sodium azide as preservative.

EXAMPLE III

A positive control serum is prepared from a pool of known hepatitis B surface antigen positive human serum. The serum is heat treated at 60° C. for about 10 hours to destroy infectivity of the virus and then two-fold serially diluted in normal human serum. The dilution used is that giving a definite 1+ reaction with the latex reagent of Example I or Example II. It is then sterile filtered and filled into sterile containers.

EXAMPLE IV

A negative control serum is produced from undiluted human serum, shown to be negative for hepatitis B surface antigen by the latex reagent of Example I or Example II and by radioimmunoassay. It is sterile filtered and filled into sterile containers.

EXAMPLE V

Human plasma which contains antibodies to hepatitis B surface antigen is titered by gel diffusion, and is converted to serum by the addition of calcium chloride and bovine thrombin. Gamma globulin is then prepared from the serum by precipitation with 16% w/v sodium sulfate. After washing the precipitate in 14% w/v sodium sulfate, it is dialyzed overnight against a low molarity phosphate buffer and passed through DEAE cellulose which had been previously equilibrated with the same buffer. The purified gamma globulin is then standardized by concentration and dialyzed against phosphate buffered saline. It is then sterile filtered and filled into sterile containers.

EXAMPLE VI

A standard solution of purified human gamma globulin in glycine buffered saline is added to a suspension of 0.2 µ polystyrene latex and heated at 57° C. for 15 minutes. The suspension, used to absorb out rheumatoid factor in test sera, is diluted in glycine buffered saline and filled into sterile containers.

EXAMPLE VII

A confirmatory test diluent is prepared by diluting a solution of 30% w/v solution bovine serum albumin with phosphate buffered saline to a 5% w/v protein concentration. The solution is then sterile filtered and filled into sterile containers.

What is claimed is:

1. In a method of testing for the presence of hepatitis B surface antigen in human blood which comprises mixing a test sample of the said blood free of red blood cells with a purified hepatitis B surface antibody coated latex diagnostic composition and observing a positive reaction, the improvement which comprises differentiating said positive reaction between a specific reaction with hepatitis B surface antigen and a nonspecific reaction due to the presence of rheumatoid factor by (a) adsorbing out the rheumatoid factor in said test sample by mixing the sample with latex beads coated with human gamma globulin, (b) mixing the adsorbed test sample with a purified antibody specific to hepatitis B surface antigen to neutralize said antigen, (c) mixing the purified hepatitis B surface antibody coated latex diagnostic composition with the mixture of step (b), and (d) observing specific inhibition of agglutination when said antigen is present.

2. The method of claim 1 wherein the diagnostic composition comprises an aqueous suspension of substantially uniform spherical polystyrene particles having a diameter of about 0.23 microns coated with purified antibody specific to said hepatitis B surface antigen, said antibody being derived from the serum of guinea pigs which have been immunized with purified hepatitis B surface antigen from human blood and said antibody being free from residual antibodies to human serum proteins, said suspension also containing in solution in the aqueous medium normal guinea pig serum which does not contain antibody specific to hepatitis B surface antigen.

3. The method of claim 1 wherein prior to the step (a) thereof additional confirmatory test steps are performed with said positive test sample which comprises, (a) adding a purified antibody specific to hepatitis B surface antigen to said test sample, (b) mixing a purified hepatitis B surface antibody coated latex diagnostic composition with the antibody-test sample mixture, (c) observing specific inhibition of agglutination where said hepatitis B surface antigen is present and (d) comparing said reaction with positive and negative controls.

4. The method of claim 3 wherein the diagnostic composition comprises an aqueous suspension of substantially uniform spherical polystyrene particles having a diameter of about 0.23 microns coated with purified antibody specific to said hepatitis B surface antigen, said antibody being derived from the serum of guinea pigs which have been immunized with purified hepatitis B surface antigen from human blood and said antibody being free from residual antibodies to human serum proteins, said suspension also containing in solution in the aqueous medium normal guinea pig serum which does not contain antibody specific to hepatitis B surface antigen.

* * * * *